United States Patent
Schulz et al.

(10) Patent No.: US 7,654,150 B2
(45) Date of Patent: Feb. 2, 2010

(54) SPECIMEN CONTAINMENT MODULE FOR ORTHOPEDIC SIMULATOR

(75) Inventors: Bradley D. Schulz, Savage, MN (US); Harold F. Fahrendorff, Golden Valley, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 263 days.

(21) Appl. No.: 11/335,974

(22) Filed: Jan. 20, 2006

(65) Prior Publication Data

US 2007/0172394 A1      Jul. 26, 2007

(51) Int. Cl.
*G01N 3/00* (2006.01)
(52) U.S. Cl. .......................... 73/856; 73/857
(58) Field of Classification Search ............... 73/788, 73/804, 856–860
See application file for complete search history.

(56) References Cited

U.S. PATENT DOCUMENTS

| | | | |
|---|---|---|---|
| 3,597,967 A | 8/1971 | Drexler et al. ............... 73/91 |
| 3,658,143 A | 4/1972 | Schwartz | |
| 3,937,071 A | 2/1976 | Slota et al. .................. 73/809 |
| 4,196,635 A | 4/1980 | Zuber et al. ................. 73/794 |
| 4,318,301 A * | 3/1982 | Justice et al. ............... 73/866 |
| 4,428,238 A | 1/1984 | Tauscher ..................... 73/663 |
| 4,676,110 A | 6/1987 | Hodo et al. .................. 73/809 |
| 4,882,677 A | 11/1989 | Curran .................. 364/413.02 |
| 5,009,523 A | 4/1991 | Folger et al. | |
| 5,014,719 A | 5/1991 | McLeod ...................... 128/774 |
| 5,151,859 A | 9/1992 | Yoshino et al. ............. 701/23 |
| 5,259,249 A | 11/1993 | Fetto ........................... 73/794 |
| 5,324,247 A | 6/1994 | Lepley ....................... 482/134 |
| 5,327,038 A | 7/1994 | Culp .......................... 310/306 |
| 5,337,758 A | 8/1994 | Moore et al. ................ 600/594 |
| 5,360,016 A | 11/1994 | Kovacevic | |
| 5,403,252 A | 4/1995 | Leon et al. .................. 482/5 |
| 5,415,661 A | 5/1995 | Holmes ...................... 606/69 |
| 5,511,431 A | 4/1996 | Hinton ........................ 73/806 |
| 5,569,858 A | 10/1996 | Askea et al. | |
| 5,670,708 A | 9/1997 | Vilendrer | |
| 5,869,328 A | 2/1999 | Antoci et al. | |
| 5,936,858 A | 8/1999 | Arai ............................ 700/30 |
| 5,937,530 A | 8/1999 | Masson ....................... 33/534 |

(Continued)

FOREIGN PATENT DOCUMENTS

DE           27 28 007         6/1977

(Continued)

OTHER PUBLICATIONS

"Biomechanical Materials Testing Laboratory" Findlers University. Aug. 7, 2007. http://som.flinders.edu.au/FUSA/ORTHOWEB/lab.htm.

(Continued)

*Primary Examiner*—Lisa M Caputo
*Assistant Examiner*—Freddie Kirkland, III
(74) *Attorney, Agent, or Firm*—Westman, Champlin & Kelly, P.A.

(57) ABSTRACT

An orthopedic simulator, such as a spinal implant wear test machine, is provided with a specimen containment module that may be removed from the machine as a unit. The releasable attachability of the specimen containment module permits remote specimen installation and reduces environmental contamination.

36 Claims, 4 Drawing Sheets

U.S. PATENT DOCUMENTS

| | | | |
|---|---|---|---|
| 5,952,582 A | 9/1999 | Akita | 73/855 |
| 5,959,215 A | 9/1999 | Ono et al. | 73/798 |
| 5,999,168 A | 12/1999 | Rosenberg et al. | 345/161 |
| 6,058,784 A * | 5/2000 | Carroll et al. | 73/856 |
| 6,171,812 B1 | 1/2001 | Smith et al. | 435/40.52 |
| 6,418,392 B1 | 7/2002 | Rust et al. | 702/123 |
| 6,447,448 B1 | 9/2002 | Shikawa et al. | |
| 6,447,518 B1 | 9/2002 | Krause et al. | 606/80 |
| 6,472,202 B1 | 10/2002 | Banes | |
| 6,502,837 B1 | 1/2003 | Hamilton et al. | 280/5.515 |
| 6,510,740 B1 | 1/2003 | Behm et al. | 73/708 |
| 6,538,215 B2 | 3/2003 | Montagnino et al. | 177/25.16 |
| 6,571,373 B1 | 5/2003 | Devins et al. | 716/5 |
| 6,581,437 B2 | 6/2003 | Chrystall et al. | 73/7 |
| 6,629,466 B2 * | 10/2003 | Grote et al. | 73/857 |
| 6,645,251 B2 | 11/2003 | Salehi et al. | |
| 6,659,200 B1 | 12/2003 | Eppink | 175/61 |
| 6,706,005 B2 | 3/2004 | Roy et al. | |
| 6,715,336 B1 | 4/2004 | Xu | 73/7 |
| 6,721,922 B1 | 4/2004 | Walters et al. | 716/1 |
| 6,860,156 B1 | 3/2005 | Cavallaro et al. | |
| 6,865,954 B2 * | 3/2005 | Zubok et al. | 73/804 |
| 7,029,475 B2 | 4/2006 | Panjabi | 606/279 |
| 7,040,177 B2 * | 5/2006 | Zubok et al. | 73/804 |
| 7,131,338 B2 * | 11/2006 | Zubok et al. | 73/804 |
| 7,204,160 B1 | 4/2007 | Sadegh et al. | 73/862.041 |
| 7,219,555 B2 * | 5/2007 | Salvesen | 73/788 |
| 7,284,446 B2 * | 10/2007 | Zubok et al. | 73/804 |
| 7,333,111 B2 | 2/2008 | Ng-Thow-Hing et al. | 345/473 |
| 7,357,038 B2 * | 4/2008 | Zubok et al. | 73/804 |
| 2001/0045941 A1 | 11/2001 | Rosenberg et al. | 345/161 |
| 2002/0029610 A1 | 3/2002 | Chrystall et al. | 73/7 |
| 2002/0166387 A1 * | 11/2002 | Grote et al. | 73/857 |
| 2002/0170361 A1 | 11/2002 | Vilendrer et al. | 73/849 |
| 2003/0029247 A1 | 2/2003 | Biedermann et al. | 73/768 |
| 2003/0053901 A1 | 3/2003 | Roy et al. | 414/735 |
| 2003/0110830 A1 | 6/2003 | Dehdashtian et al. | |
| 2004/0019382 A1 | 1/2004 | Amirouche et al. | 623/18.11 |
| 2004/0019384 A1 | 1/2004 | Kirking et al. | |
| 2005/0056099 A1 | 3/2005 | Zubok et al. | |
| 2005/0241404 A1 | 11/2005 | Salvesen | |

FOREIGN PATENT DOCUMENTS

| | | |
|---|---|---|
| DE | 44 11 508 A1 | 2/1994 |
| EP | 0 919 201 A1 | 9/1998 |
| GB | 1108652 A | 4/1968 |

OTHER PUBLICATIONS

Prosthetic Knee Tester, 6 Station Knee Simulator. ATMI-Boston, Nov. 6, 2005, Retrieved from the Internet http://web.archive.org/web/20051106111417/http://www.amtiweb.com/sim/knee_machine1.htm> entire document.

Official Search Report of the US Patent Office in counterpart foreign application No. PCT/US07/00727 filed Jan. 10, 2007.

Written Opinion of the US Patent Office in counterpart foreign application No. PCT/US07/00727 filed Jan. 10, 2007.

Official Search Report of the US Patent Office in counterpart foreign application No. PCT/US07/00733 filed Jan. 10, 2007.

Written Opinion of the US Patent Office in counterpart foreign application No. PCT/US07/00733 filed Jan. 10, 2007.

Official Search Report of the US Patent Office in counterpart foreign application No. PCT/US07/00796 filed Jan. 10, 2007.

Written Opinion of the US Patent Office in counterpart foreign application No. PCT/US07/00796 filed Jan. 10, 2007.

Official Search Report of the US Patent Office in counterpart foreign application No. PCT/US07/00797 filed Jan. 10, 2007.

Written Opinion of the US Patent Office in counterpart foreign application No. PCT/US07/00797 filed Jan. 10, 2007.

Official Search Report of the US Patent Office in counterpart foreign application No. PCT/US07/00799 filed Jan. 10, 2007.

Wirtten Opinion of the US Patent Office in counterpart foreign application No. PCT/US07/00799 filed Jan. 10, 2007.

International Preliminary Report on Patentability PCT/US07/00727 dated Jul. 15, 2008; one page.

PCT International Search Report and Written Opinion of the International Searching Authority, PCT/US2004/040798 dated Jun. 4, 2005; one page.

* cited by examiner

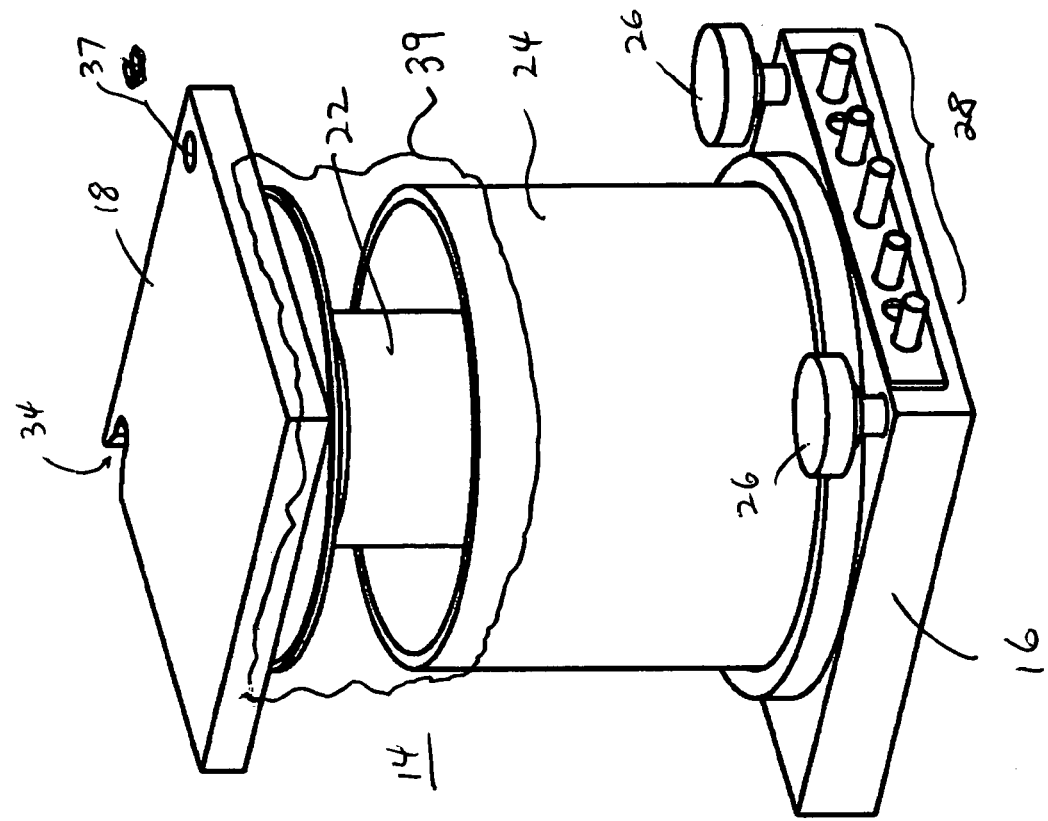
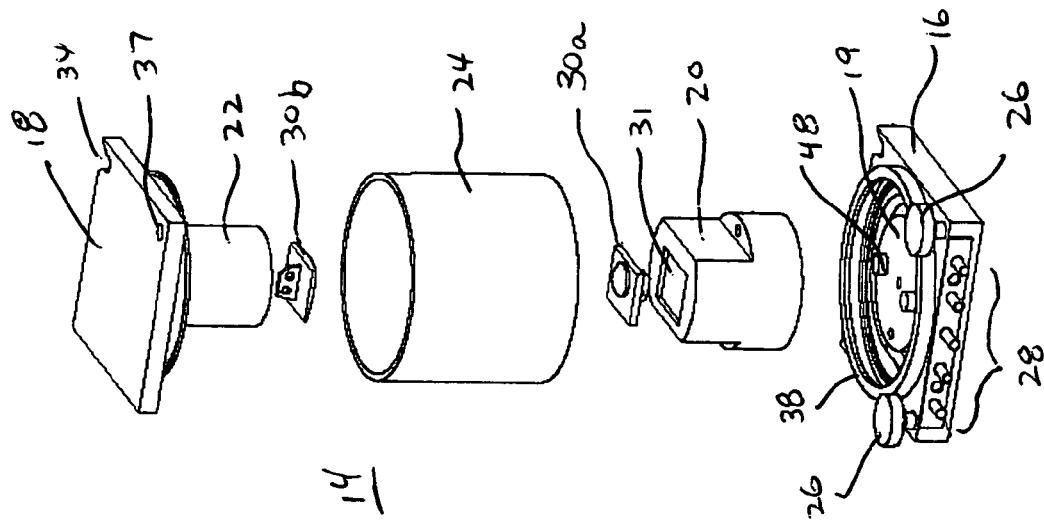

SPECIMEN CONTAINMENT MODULE FOR ORTHOPEDIC SIMULATOR

FIELD

The disclosure relates to the field of orthopedic simulators, and more particularly, to orthopedic specimen containers for use in an orthopedic simulator that performs testing of orthopedic test specimens.

BACKGROUND

There is an ever-increasing demand for orthopedic devices and prosthetic implants. These devices and implants need to be tested prior to their use within the human body. Testing standards have been or are being formulated for the testing that such devices must undergo. For example, the wear of an orthopedic device, such as a spinal implant, is a critical parameter that needs to be fully tested. For testing the wear of such an orthopedic device, an orthopedic simulator may be employed to subject the orthopedic device to a large number of duty cycles that simulate the motion that the orthopedic device is likely to be subjected to after implantation into a body.

For an orthopedic device, such as a spinal implant, the wear testing may take place in a container or chamber that contains a fluid bath that essentially simulates the internal environment within a body. For example, with a spinal implant, bovine fluid is specified as the fluid in which the test specimen is immersed.

In preparing a specimen for testing within an orthopedic simulator, which will apply various forces along and around different axes, the test specimen will be typically coupled at a test station to the various test machine components which will apply the forces to the test specimen. It is usually a very laborious and difficult process to install a test specimen into a test station. The orthopedic simulators are complicated machines, and access to the holders or adapters for the test specimen is very limited and awkward. Exacerbating this issue, test specimens are often very delicate and the careful removal and insertion of test specimens requires great expertise and a deft touch in order to install the test specimens directly onto the orthopedic simulators.

Once properly installed, and following the application of various forces over millions of cycles in a wear test, the test specimen needs to be inspected for the signs of wear. This includes examining the test specimen and the fluid in which the specimen was immersed for contamination particles. The presence of such particles reveals wearing. A concern with the in situ installation of test specimens at the orthopedic simulators is the potential for contamination of the fluid so that the results of the wear test may be easily compromised.

Another concern with the mounting of test specimens in situ at orthopedic simulators are the difficulties in mounting one-piece specimens. The mounting of such test specimens has proven particularly difficult with conventional orthopedic simulators.

SUMMARY

There is a need for an arrangement that allows for remote preparation of a test specimen and a subsequent releasable attachment to a testing machine, such as an orthopedic simulator, for testing purposes.

These and other needs are met by embodiments of the present invention which provide a specimen containment module comprising a specimen chamber for receiving a specimen, and a module interface that holds the specimen chamber and is configured for releasably attaching the module to a test machine while holding the specimen chamber.

The earlier stated needs are also met by other embodiments of the present invention which provide an orthopedic device test machine comprising at least one force applicator configured to apply force to an orthopedic device test specimen, and a specimen containment module configured to secure the test specimen and which is releasably attachable to the test machine with the secured test specimen.

The earlier stated needs are also met by still further embodiments of the present invention which provide a method of testing an orthopedic device comprising the steps of securing the orthopedic device and modular unit remotely from a test machine, and releasably attaching the modular unit containing the secured orthopedic device into the test machine.

The foregoing and other aspects, features and advantages of embodiments of the present invention will become more apparent from the following detailed description and accompanying drawings.

BRIEF DESCRIPTION OF THE DRAWINGS

FIG. 2 is an exploded perspective view of a specimen containment module constructed in accordance with embodiments of the present invention.

FIG. 3 depicts the specimen containment module of FIG. 2 in an assembled view and in isolation.

DETAILED DESCRIPTION

The embodiments of the present invention address and solve problems related to the preparation, insertion and removal of test specimens in orthopedic simulators or other such devices. In particular, the embodiments of the invention address concerns related to careful preparation of test specimens at the bench-top, the potential damage during removal and insertion of delicate test specimen samples, mounting of one-piece specimens, and the potential for contamination of the test fluid. These concerns are addressed and solved, at least in part, by embodiments of the present invention which provide, for example, an orthopedic device test machine, such as a simulator, in which at least one force applicator is configured to apply force to the orthopedic device test specimen. The specimen containment module is configured to secure the test specimen remotely. The specimen containment module may then be releasably attached to the test machine while it holds the secured test specimen. This allows for the preparation work on the specimen to be performed at the bench-top. Also, a removable and releasably attachable specimen containment module allows for the careful removal and insertion of delicate test samples. Contamination potential is greatly reduced since the sample may be prepared and the specimen containment module sealed prior to installation at the test device. After testing, the specimen containment module may be readily detached from the test machine and removed to a clean room for determining the wear of the orthopedic device. Additionally, the separable nature of the specimen containment module facilitates the mounting of one-piece specimens, as well as facilitating the mounting of specimens in general. It is much easier to mount specimens at the specimen containment module on a workbench, rather than mounting them in situ at the orthopedic device test machine.

Figure 1:
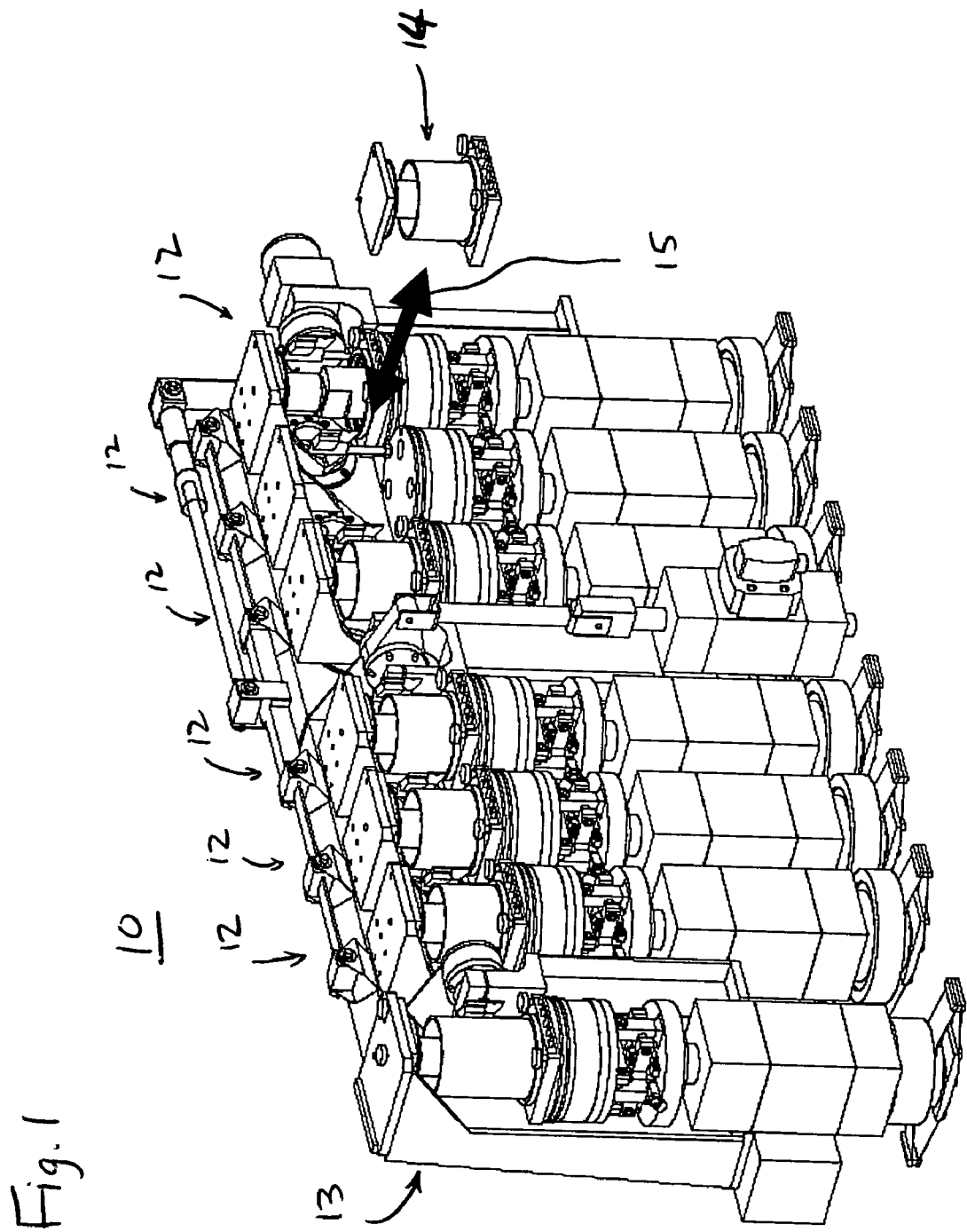
FIG. 1 is a front perspective view of an orthopedic simulator constructed in accordance with embodiments of the present invention showing the insertability and removability of a specimen containment module in accordance with embodiments of the present invention.

FIG. 1 is a perspective view of an orthopedic device test machine, such as an orthopedic simulator. The test machine 10, which may be a spinal wear implant test machine, for example, is able to provide forces Fx, Fy and Fz in the x, y and z directions. Additionally, torques may be applied around the x, y and z axes. The axes and motions are not depicted in FIG. 1, so as not to obscure the present invention.

The test machine 10 has a plurality of test stations 12. In the embodiment of FIG. 1, there are six stations 12 in which specimens are subjected to the forces applied by the machine 10, and a control station 13 that holds the specimen that is not subjected to all of the forces provided at the other test stations 12.

It should be apparent to those of ordinary skill in the art that although the test machine 10 is being described as a spinal implant wear test machine for descriptive purposes, it is to be clearly understood that this is by way of illustration and example only and is not to be taken by way of limitation. The test machine 10 may be configured for other orthopedic simulation, such as simulating hip motion and forces for prosthetic hips, knee joints, etc.

The test machine 10 in FIG. 1 is depicted as having a specimen containment module 14 removed from one of the test stations 12. The arrow 15 shows the direction of installation and removal of the specimen containment module 14. The removal of the specimen containment module 14 as a unit helps to avoid environmental contamination, eases inspection, and simplifies specimen installation, as will be described in more detail.

FIG. 2 shows the specimen containment module 14 in an exploded view, while FIG. 3 depicts an assembled specimen containment module 14 with in a sealed condition. The module 14 includes a base 16 and an upper connector 18. The base 16 and the upper connector 18 are releasably attached during installation to the test machine 10. The chamber base 16 may be made of any suitable material, such as Delrin® or other suitable material. A specimen mounting platform 19 is configured with features, such as pins 48, that help to pilot and provide anti-rotation functionality for the mounting of a lower specimen adapter 20. The specimen adapter 20 is particularly configured for holding a specific test specimen, in certain preferred embodiments. For example, in FIG. 2, a lower portion 30a of a test specimen fits precisely within a recess 31 in the lower specimen adapter 20. The specimen containment module may either contain the lower specimen adapter 20 or this adapter 20 may be provided by the manufacturer of the test specimen 30.

The base 16 also includes a recess 32 that is open-ended that interacts with a pin 40 at the test station 12 to allow a sliding installation of the specimen containment module 14 at the test station 12. Recesses 36 permit releasable fasteners 26, such as thumb screws, to provide an anchoring in the x and y directions, as well as providing clamping in the z direction.

The upper connector 18 includes a slot 34 that is similar to slot 32 in the base 16. An additional recess 37 is similar to those recesses 36 in the base 16. The upper connector 18 may be releasably attached to the test machine 10.

An upper specimen adapter 22 is attached to the upper connector 18 by any suitable means. The upper specimen adapter 22 is configured to retain an upper portion 30b of the test specimen. As such, the upper specimen adapter 22 may also be provided by the maker of the test specimen.

The base 16 includes a retaining ring 38 that projects upwardly from the surface of the base 16. A chamber 24 which may be made of clear acrylic, for example, is placed concentrically within the retaining ring 38 following the securing of the lower specimen adapter 20 that holds the lower portion 30a of the test specimen into the base 16. Together, the chamber 24 and the base 16 form a fluid container suitable for retaining a bath, such as bovine fluid, in which the test specimen 30 is immersed during testing.

In certain embodiments, tubing 44 is provided that extends through the base 16 to provide a temperature control. This tubing 44 serves as a test fluid temperature control element. In the embodiment illustrated in FIG. 4, the fluid circulation tube 46 provides a temperature control fluid that may precisely maintain the bath contained within the fluid container 16, 24 at a precise temperature. The control for such a fluid temperature arrangement is not shown. A temperature probe 42 is provided to provide feedback of the temperature in the bath.

Figure 4:
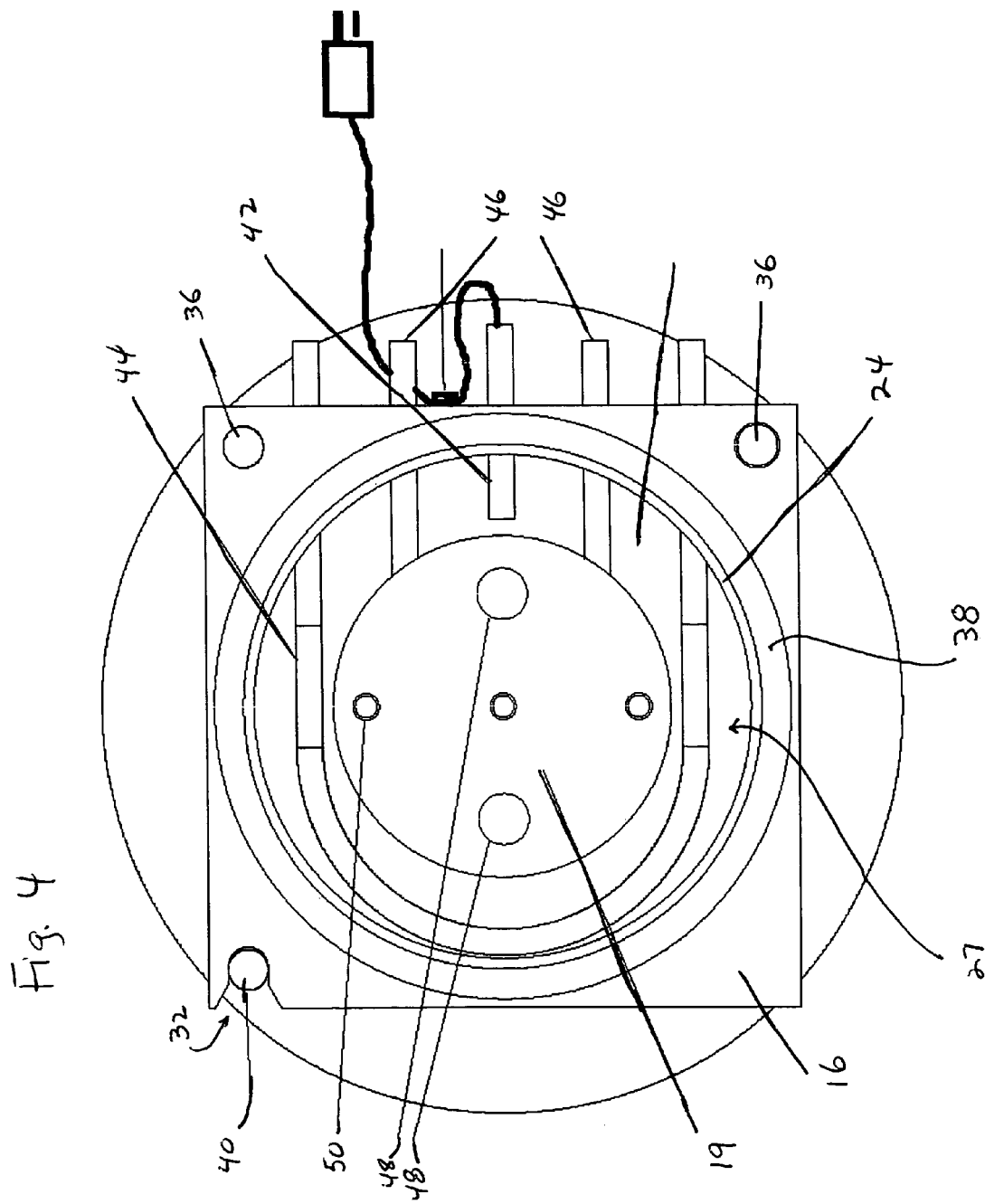
FIG. 4 is a top view of a cross-section of the specimen containment module of FIG. 3.

In FIG. 4, bath fluid circulation tubes 46 are depicted that may be employed to circulate the bath in which the specimen is immersed during a test. The fluid may be circulated from test station to test station in one circulation loop. However, in certain other embodiments, which are specially preferred, the bath fluid is not circulated but remains in individual loops in a non-circulating fashion. This prevents cross-contamination between test stations and other concerns.

Following placing the chamber 24 on the base 16 within the retaining ring 38, the upper connector 18 and upper specimen adapter 22 may be placed in the assembled position as shown in FIG. 3. In this manner, the upper and lower portions 30a, 30b of the test specimen are placed into contact with one another. Bovine fluid or other test fluid may then fill the fluid container created by the base 16 and the chamber 24 and into a moat 27. Following the filling of the fluid container 16, 24, the specimen containment module 14 may be sealed, such as by a plastic flexible seal 39 that extends between the base 16 and the upper container 18 and which circumscribes the chamber 24. The seal 39 allows the specimen containment module 14 to be prepared remotely from the test machine 10 and sealed against the environment during: transport of the specimen containment module 14 to the test machine 10, installation of the specimen containment module 14 in a test station 12, through the duration of a test, removal of the specimen containment module 14 from the test station 12 and transport to a clean room or other remote environment where the seal 39 may be safely removed without threat of contamination. This sealed aspect of embodiments of the present invention thereby provide mobility and ease of handling of the test specimen without compromising the fluid or the test specimen.

Figure 5:
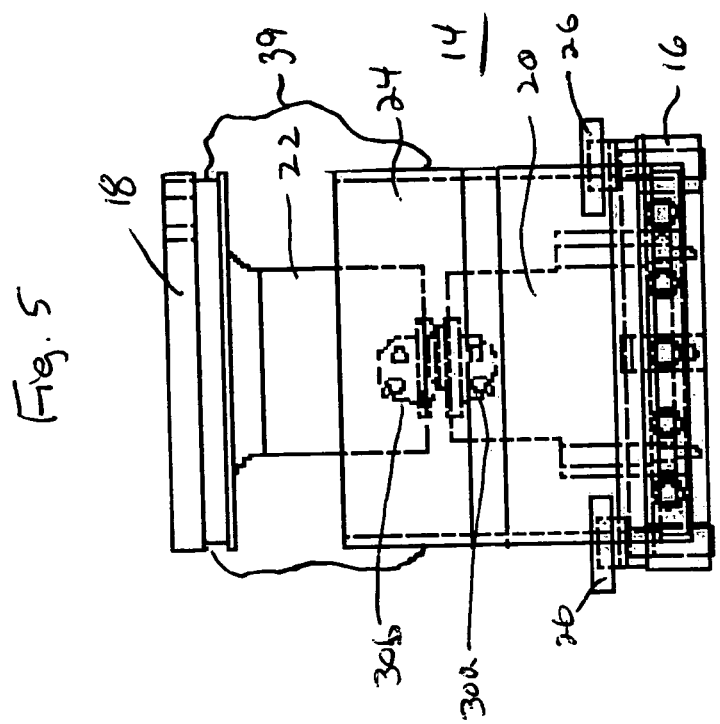
FIG. 5 is a side cross-sectional view of the specimen containment module of FIGS. 2-4.
Figure 6:
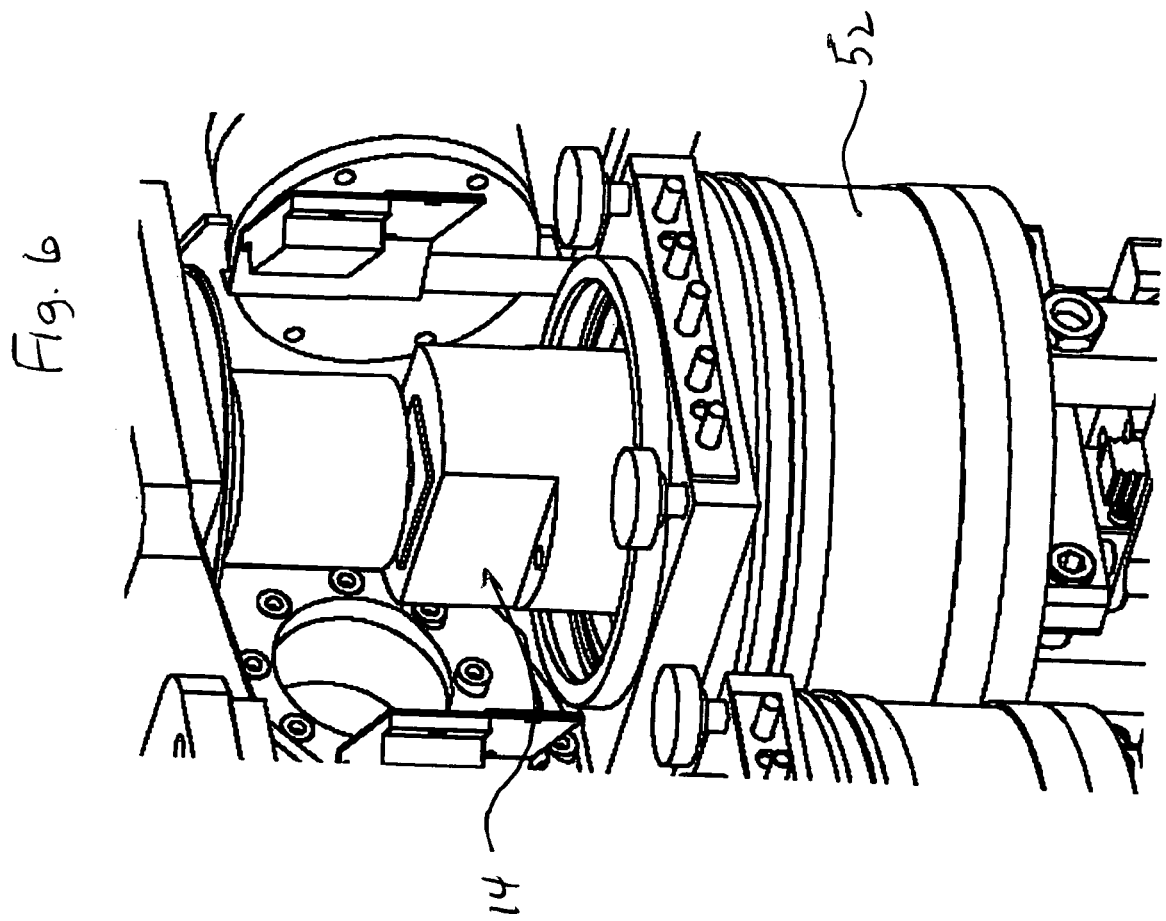
FIG. 6 shows the specimen containment module, without a chamber for illustrative purposes, in an installed position within an orthopedic simulator of FIG. 1.

FIG. 5 depicts the specimen containment module 14 in an assembled state, with a test specimen 30 retained between the upper specimen adapter 22 and the lower specimen adapter 20, for example. This specimen 30 is exemplary only, as types of test specimens and orthopedic devices other than spinal implants may be employed without departing from the scope of the invention.

It should be apparent that the specimen containment module as depicted in the figures allows for careful removal and insertion of the test specimens, which may be extremely delicate in certain examples. This allows the preparation work for the specimen to be performed at a bench-top in a clean room, rather than at the test machine itself, which may introduce many contaminants into the environment, such as oil, etc. Further, the remote nature of the mounting process facilitates the mounting of one-piece specimens, such as where the inferior and superior portions of a test specimen are permanently joined. Contamination potential is greatly reduced since the preparation of the test specimen 30 may be performed in a clean room and especially remotely from the test machine 10 itself. The specimen containment module 14 may also be employed to test many different types of test specimens, with a change of upper and lower adapters 22, 20 providing secure retention of different types of test specimens. Finally, once testing is completed, the releasable attachment capability of the specimen containment module allows the entire specimen containment module 14 to be removed from the test machine environment which prevents environmental contamination while easing the inspection and determination of the wear characteristics of the test specimen.

It should be noted that other types of releasable fasteners, such as snap connections or other releasable fasteners may be employed without departing from the scope of the present invention.

Hence, after assembly and securement of the test specimen 30 within the specimen containment module 14 remotely from the test machine 10, an installation process is performed to install the specimen containment module 14 in the test station 12 of the test machine 10. A specimen containment module 14, serving as a modular unit, may be slid in the direction of arrow 15 as depicted in FIG. 1 into the test station 12. The locating pins (not shown in FIG. 1, but shown as pin 32 in FIG. 4) interact with the recesses 32, 34 in the base 16 and upper connector 18 as the specimen containment module 10 is slid into the test station 12. When the recesses 36 and 37 in the base 16 and the upper connector 18 are aligned with corresponding recesses in the test machine 10, releasable fasteners 26 releasably attach the specimen containment module 14 to the test machine 10. Appropriate testing may then be performed, with forces being applied to the test specimens 30a, 30b through the upper specimen adapter 22 and the lower specimen adapter 20.

Following the testing, which may be performed over millions of load cycles, the specimen containment module 14 may be removed by removing the releasable fasteners 26 and sliding the specimen containment module 14 as a modular unit from the test station 10. The specimen containment module 14 may then be detached from the test machine 10 and inspection and determination of the wearing of the specimen may be then performed in a manner that avoids contamination.

The releasably attachable specimen containment module of the embodiments of the present invention, including the orthopedic device test machine that employs such a specimen containment module, allows for removal of the specimen containment module from the machine as a unit to avoid environmental contamination, ease inspection, and simplify specimen installation, among other advantageous benefits.

Although the present invention has been described and illustrated in detail, it is to be clearly understood that the same is by way of illustration and example only and is not to be taken by way of limitation, the scope of the present invention being limited only by the terms of the appended claims.

What is claimed:

1. A module assembly connectable to first and second portions of a test apparatus comprising:
   a holder assembly including a first specimen holder coupled to a base platform configured to hold a first portion of a test specimen and a second specimen holder configured to hold a second portion of the test specimen coupled to an upper platform wherein connection of the test specimen to the first specimen holder and the second specimen holder forms a module unit comprising the base platform and the upper platform coupled to the base platform via connection of the test specimen to the first and second specimen holders;
   a specimen chamber disposed between the upper and base platforms of the module unit; and
   at least one fastener element configured to releasably connect the module unit having the test specimen secured to the first and second specimen holders to at least one of the first or second portions of the test apparatus.

2. The module assembly of claim 1 and comprising an enclosure coupled to the base platform to form the specimen chamber.

3. The module assembly of claim 2 and further comprising a flexible enclosure portion between the enclosure and the upper platform to seal the specimen chamber.

4. The module assembly of claim 1 wherein the base platform and the upper platform each include at least one fastener opening to releasably connect the base platform and the upper platform to the first and second portions of the test apparatus to releasably connect the module unit to the test apparatus.

5. The module assembly of claim 1 wherein the specimen chamber is configured to hold a test fluid.

6. The module assembly of claim 5 further comprising a test fluid temperature control element.

7. The module assembly of claim 6, wherein the test fluid temperature control element includes a fluid circulation tube through which a temperature control fluid is circulated.

8. The module assembly of claim 5 wherein the base platform includes an inlet and an outlet to the specimen chamber and the test fluid is circulated into and out of the specimen chamber through the inlet and the outlet.

9. A module assembly connectable to a test apparatus comprising:
   a holder assembly including a first specimen holder configured to hold a first portion of a test specimen and a second specimen holder configured to hold a second portion of the test specimen;
   a base platform and a upper platform wherein the first specimen holder is coupled to the base platform and the second specimen holder is coupled to the upper platform;
   a specimen chamber disposed between the upper and base platforms; and
   at least one fastener element configured to releasably connect the module assembly to the test apparatus wherein the module assembly is slidably inserted between spaced first and second portions of the test apparatus and including at least one slot having a pin slideable in the at least one slot to align the module assembly for connection to the test apparatus.

10. The module assembly of claim 9 wherein the at least one slot is formed in at least one of the base platform or the upper platform.

11. The module assembly of claim 10 including at least one slot formed in the base platform and at least one slot formed in the upper platform and including at least one pin slideable in the at least one slot formed in the base platform and at least one pin slideable in the at least one slot formed in the upper platform.

12. A combination comprising:
   a test apparatus configured to supply a test force or load to a test specimen and including a first portion and a second portion spaced from the first portion;
   a module assembly including a first specimen holder coupled to a first platform and a second specimen holder coupled to a second platform and the first platform being connected to the second platform through connection of a test specimen to the first and second specimen holders to form a module unit and the module unit being removably insertable between the first and second portions of the test apparatus and connectable to at least one of the first or second portions of the test apparatus by at least one fastening element.

13. The combination of claim 12 wherein the module assembly includes a specimen chamber configured to contain the test specimen and hold test fluid.

14. The combination of claim 13 wherein the specimen chamber comprising an inlet and an outlet through which the test fluid is circulated into and out of the specimen chamber.

15. The test combination of claim 13 wherein the module assembly further includes a temperature control element that controls a temperature of the test fluid in the specimen chamber.

16. The combination of claim 15 wherein the temperature control element includes a fluid circulation tube through which a temperature control fluid is circulated.

17. The test combination of claim 12 wherein the test apparatus is a spinal implant wear test machine and the test specimen is a spinal implant.

18. The combination of claim 12 wherein the first platform and the second platform of the modular unit are connectable to the first and second portions of the test apparatus by a plurality of fastening elements.

19. The combination of claim 12 wherein each of the first platform and the second platform include at least one fastener opening and further comprising a first fastener insertable into the at least one fastener opening of the first platform and a second fastener insertable into the at least one fastener opening of the second platform to secure the first platform and the second platform to the first and second portions of the test apparatus.

20. The combination of claim 12 and comprising a first enclosure portion connected to the first platform and a second flexible enclosure portion between the first enclosure portion coupled to the first platform and the second platform to form a sealed specimen chamber for the test specimen.

21. The combination of claim 12 and comprising at least one pin slidable into at least one slot to align the module unit for connection to the at least one of the first or second portions of the test apparatus.

22. The combination of claim 21 wherein the at least one slot is formed on the first platform or the second platform.

23. The combination of claim 21 including a first pin slideable into a slot in the first platform and a second pin slideable into a slot of the second platform to align the module unit between the first and second portions of the test apparatus.

24. A method of testing a test specimen, comprising the steps of:
connecting a first test specimen portion to a first specimen holder and a second test specimen portion to a second specimen holder to form a modular unit;
inserting the modular unit including the first test specimen portion secured to the first specimen holder and the second test specimen portion secured to the second specimen holder between opposed first and second portions of a test apparatus;
connecting the modular unit to the test apparatus after connecting the first test specimen portion and the second test specimen portion to the first and second specimen holders; and
applying a load or force to the test specimen secured to the first and second specimen holders of the modular unit.

25. The method of claim 24 wherein the module unit includes a fluid chamber and further comprising supplying the fluid chamber with a test fluid.

26. The method of claim 25 further comprising coupling the modular unit to a temperature control unit to circulate temperature control fluid within the fluid chamber during testing.

27. The method of claim 25 and comprising:
circulating the test fluid into and out of the fluid chamber.

28. The method of claim 24 further comprising
sealing a specimen chamber of the modular unit after connecting the first and second test specimen portions to the first and second specimen holders and prior to connecting the modular unit to the test apparatus.

29. The method of claim 24, wherein the first specimen holder is coupled to a first platform and the second specimen holder is coupled to a second platform and comprising the step of
connecting the first platform to the first portion of the test apparatus after connecting the first test specimen portion to the first specimen holder; and
connecting the second platform to a second portion of the test apparatus spaced from the first portion of the test apparatus after connecting the second test specimen portion to the second specimen holder.

30. The method of claim 24 wherein inserting the module unit comprising:
engaging one or more pins in one or more slots to align a first platform having the first specimen holder coupled thereto and a second platform having the second specimen holder coupled thereto relative to the first and second portions of the test apparatus.

31. The method of claim 24 and further comprising:
disconnecting the modular unit from the test apparatus following testing.

32. The method of claim 24 and comprising
connecting a first platform coupled to the first specimen holder and a second platform coupled to the second specimen holder through a one piece test specimen attached to the first and second specimen holders; and
connecting at least one of the first or second platforms to the first or second portions of the test apparatus.

33. The method of claim 24 and comprising:
disconnecting the module unit from the test apparatus; and
disconnecting the first test specimen portion from the first specimen holder and the second test specimen portion from the second specimen holder after disconnecting the module unit from the test apparatus.

34. A kit comprising:
a first specimen holder coupled to a first platform;
a second specimen holder coupled to a second platform; and
at least one fastener element and wherein a test specimen is connected to the first and second specimen holders and wherein the first platform having the first specimen holder is coupled to the second platform having the second specimen holder to form a module unit comprising the first and second specimen holders coupled to the first and second platforms and the module unit is connectable by the at least one fastener element to a test apparatus to test the test specimen.

35. The kit of claim 34 wherein a one piece test specimen is connected to the first and second specimen holders to form the module unit.

36. The kit of claim 34 and comprising an enclosure assembly coupled to the first and second platforms to form the module unit.

* * * * *

UNITED STATES PATENT AND TRADEMARK OFFICE
CERTIFICATE OF CORRECTION

| | | |
|---|---|---|
| PATENT NO. | : 7,654,150 B2 | Page 1 of 1 |
| APPLICATION NO. | : 11/335974 | |
| DATED | : February 2, 2010 | |
| INVENTOR(S) | : Schulz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 340 days.

Signed and Sealed this

Twenty-third Day of November, 2010

David J. Kappos
*Director of the United States Patent and Trademark Office*